(12) United States Patent
Tepper et al.

(10) Patent No.: US 10,080,876 B2
(45) Date of Patent: Sep. 25, 2018

(54) DEVICE AND METHOD FOR DRUG EVALUATION AND LOCAL TREATMENT

(75) Inventors: Robert I. Tepper, Weston, MA (US); Russell Hirsch, Los Altos Hills, CA (US); Jason E. Fuller, Boston, MA (US); Jessica L. Duda, Boston, MA (US); Craig Muir, Davis, CA (US); Jeffrey S. Ross, Lebanon Springs, NY (US); J. Christopher Flaherty, Topsfield, MA (US)

(73) Assignee: Kibur Medical, Inc., Boston, MA (US)

( * ) Notice: Subject to any disclaimer, the term of this patent is extended or adjusted under 35 U.S.C. 154(b) by 727 days.

(21) Appl. No.: 13/060,040

(22) PCT Filed: Aug. 20, 2009

(86) PCT No.: PCT/US2009/054490
§ 371 (c)(1),
(2), (4) Date: Apr. 26, 2011

(87) PCT Pub. No.: WO2010/022252
PCT Pub. Date: Feb. 25, 2010

(65) Prior Publication Data
US 2011/0230736 A1 Sep. 22, 2011

Related U.S. Application Data

(60) Provisional application No. 61/090,836, filed on Aug. 21, 2008.

(51) Int. Cl.
*A61B 10/02* (2006.01)
*A61M 37/00* (2006.01)
(Continued)

(52) U.S. Cl.
CPC ......... *A61M 31/002* (2013.01); *A61B 5/1455* (2013.01); *A61B 5/14532* (2013.01);
(Continued)

(58) Field of Classification Search
CPC . A61B 5/1455; A61B 5/14532; A61B 17/205; A61B 5/14551; A61B 5/14;
(Continued)

(56) References Cited

U.S. PATENT DOCUMENTS 5,139,832 A 8/1992 Hayashi
5,189,110 A 2/1993 Ikematu
(Continued)

FOREIGN PATENT DOCUMENTS

CA 2696209 2/2009
WO 0074767 12/2000
(Continued)

OTHER PUBLICATIONS

Bates, et al., "New amorphous thin-film lithium electrolyte and rechargeable microbattery", IEEE 35th International Power Sources Symposium, 337-39 (1992).
(Continued)

*Primary Examiner* — Eric Winakur
*Assistant Examiner* — Chu Chuan (JJ) Liu
(74) *Attorney, Agent, or Firm* — Pabst Patent Group LLP

(57) ABSTRACT

Described here are devices, systems, and kits for delivering substances to tissues. The devices generally include one or more chambers (102) and a reservoir (108) within each chamber. The reservoir may locally deliver a microdose amount of a substance to a target tissue. In some variations, a microdose amount is used in early human studies, e.g., before a phase I clinical trial, to evaluate the effect of the substance on a target tissue, or to obtain pharmacokinetic or metabolic data. In other variations, a microdose amount is used to locally treat a medical condition. In yet other variations, a microdose amount is used to locally deliver a contrast agent for a structural or functional imaging proce-
(Continued)

dure. Methods for delivering and retrieving the devices from the target tissue are also described.

23 Claims, 5 Drawing Sheets

(51) Int. Cl.
*A61B 5/00* (2006.01)
*A61M 31/00* (2006.01)
*A61B 5/145* (2006.01)
*A61B 5/1455* (2006.01)

(52) U.S. Cl.
CPC .............. *A61B 5/415* (2013.01); *A61B 5/418* (2013.01); *A61B 5/4839* (2013.01); *A61M 37/0015* (2013.01); *A61M 2037/0023* (2013.01); *A61M 2037/0061* (2013.01)

(58) Field of Classification Search
CPC ... A61B 5/1405; A61B 5/1411; A61B 5/4836; A61B 5/4839; A61B 5/14514; A61B 5/1459; A61M 39/0208; A61M 5/20; A61M 5/1452; A61M 5/3287; A61M 5/00; A61M 5/142; A61M 5/145; A61M 37/0015; A61M 2037/0023; A61M 2037/003; A61M 2037/0038; A61M 2037/0046
USPC ....... 600/309, 310, 316, 322, 344, 473, 476; 604/93.01, 272, 154, 155, 191, 890.1, 604/891.1, 892.1, 131, 151, 153, 156, 21
See application file for complete search history.

(56) References Cited

U.S. PATENT DOCUMENTS

| | | | | |
|---|---|---|---|---|
| 5,733,925 | A * | 3/1998 | Kunz et al. | 514/449 |
| 6,428,504 | B1 | 8/2002 | Riaziat | |
| 6,527,762 | B1 * | 3/2003 | Santini, Jr. | A61K 9/0009 604/890.1 |
| 6,611,707 | B1 * | 8/2003 | Prausnitz | A61B 5/1411 604/21 |
| 6,692,456 | B1 * | 2/2004 | Eppstein et al. | 604/22 |
| 8,349,554 | B2 | 1/2013 | Bahrami | |
| 8,475,412 | B2 | 7/2013 | Bahrami | |
| 1,417,802 | A1 | 2/2014 | Bahrami | |
| 8,657,786 | B2 | 2/2014 | Bahrami | |
| 8,672,887 | B2 | 3/2014 | Bahrami | |
| 8,834,428 | B2 | 9/2014 | Bahrami | |
| 2006/0058966 | A1 | 3/2006 | Bruckner | |
| 2006/0094985 | A1 * | 5/2006 | Aceti et al. | 600/575 |
| 2006/0163215 | A1 | 7/2006 | Maenosono | |
| 2007/0275035 | A1 * | 11/2007 | Herman | A61K 9/0024 424/426 |
| 2008/0108959 | A1 * | 5/2008 | Jung et al. | 604/272 |
| 2012/0109104 | A1 | 5/2012 | Bahrami | |
| 2012/0121514 | A1 * | 5/2012 | Bahrami et al. | 424/9.2 |
| 2012/0265064 | A1 | 10/2012 | Bahrami | |
| 2012/0296206 | A1 | 11/2012 | Bahrami | |
| 2013/0184593 | A1 | 7/2013 | Tepper | |
| 2014/0162360 | A1 | 6/2014 | Bahrami | |
| 2014/0162901 | A1 | 6/2014 | Bahrami | |

FOREIGN PATENT DOCUMENTS

| | | |
|---|---|---|
| WO | 2004047907 | 6/2004 |
| WO | 2005025413 | 3/2005 |
| WO | 2008008557 | 1/2008 |
| WO | 2008010681 | 1/2008 |

OTHER PUBLICATIONS

Di Masi, et al., "The Price of Innovation: New Estimates of Drug Development Costs", J. Hlth. Econ., 22: 151-185 (2003).
Fire, et al, "Potent and specific genetic interference by double-stranded RNA in Caenorhabditis elegans", Nature, 391:806-11 (1998).
Jones and Akridge, "Development and performance of a rechargeable thin-film solid-state microbattery", J Power Sources, 54:63-67 (1995).
Laske, et al., "Efficacy of direct intraturnoral therapy with targeted protein toxins for solid human glkiomas in nude mice", J Neurosurg., 80:520-6 (1994).
Sheu, et al., "Small hepatocellular carcinoma: intratumor ethanol treatment using new needle and guidance systems", Radiology, 163:43-8 (1987).
Weissleder, et al., "In vivo imaging of tumors with protease-activated near-infrared fluotescent probes", Nature, 17:375-8 (1999).

* cited by examiner

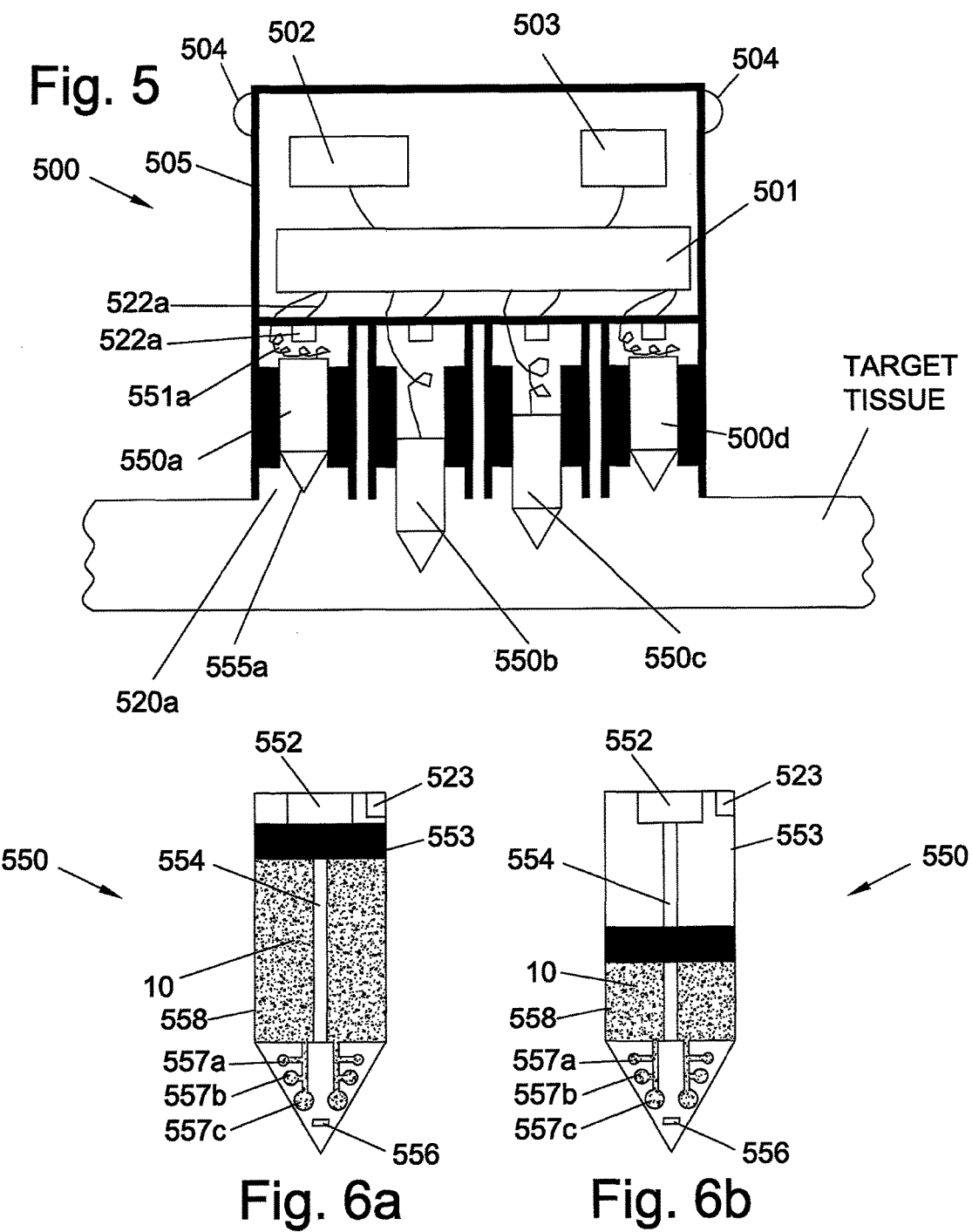

DEVICE AND METHOD FOR DRUG EVALUATION AND LOCAL TREATMENT

RELATED APPLICATIONS

This application is a national phase filing under 35 U.S.C. § 371 of PCT/US2009/054490 filed under the Patent Cooperation Treaty on Aug. 20, 2009, which claims benefit of and priority to U.S. Provisional Patent Application No. 61/090,836, filed on Aug. 21, 2008, the contents of each being hereby incorporated by reference in their entirety.

FIELD

Described here are devices, systems, and kits for the early evaluation of substances in humans. Specifically, devices that locally deliver microdose amounts of the substances are described. Methods for assessing the effect of the substances on a target tissue, as well as delivery and retrieval of the devices from the target tissue are also described. Devices that locally release substances to aid diagnosis of various medical conditions are further described.

BACKGROUND

Understanding the metabolism or efficacy of a candidate drug is crucial in determining whether the drug can be commercialized. Current methods of investigating such drug aspects before entering human studies rely heavily on animal and in vitro models. Thus, when taking drugs into humans for the first time, there is a concern that drug metabolism pathways, effect on target tissues and organs, pharmacokinetics, etc., might differ substantially from those predicted from the model studies. Some of these differences are of no practical consequence, while others are so serious that the development program must be abandoned. Information about efficacy and metabolism is also useful in determining the optimal drug or drug combination to use in treating a given patient.

Given that the results of currently available methods for screening candidate compounds are unpredictable, drug development is a long, complex, and expensive endeavor. Typical development times may be between 10 and 15 years. Furthermore, the cost of developing a newly marketed drug may reach between about one to two billion dollars (Di Masi, J. A. et al. The Price of Innovation: New Estimates of Drug Development Costs. *J. Hlth. Econ.*, Vol. 22: 151-185 (2003)).

In view of the importance of drug development in treating medical conditions, devices having improved predictability would be useful. Devices for obtaining profiles of candidate drug data in humans would be desirable. In particular, devices capable of providing human data on the local effect of a drug candidate on the target tissue or organ would be desirable.

SUMMARY

Described here are devices, systems, methods and kits for delivering substances to tissues. The devices generally include one or more chambers and a reservoir within each chamber. The reservoir may locally deliver a microdose amount of a substance to a target tissue. The term "tissue" as used herein generally refers to groups of cells that perform a particular function, including bodily fluids such as blood, lymph, and saliva, as well as organs, which are aggregates of tissues. By "locally" it is meant administration or delivery to a target tissue location from a source that is at the target tissue location, or adjacent to or in close proximity to the target tissue location. As used herein, "microdose" refers to an amount of a substance that is locally delivered to a tissue to determine one or more parameters, such as efficacy or metabolism, of the substance. In some variations, a microdose amount is used in early human studies, e.g., before a phase I clinical trial, to evaluate the effect of the substance on a target tissue, or to obtain pharmacokinetic or metabolic data. In other variations, a microdose amount is used to locally treat a medical condition, e.g., a cancer or tumor. In yet other variations, a microdose amount is used to locally deliver a contrast agent for a structural or functional imaging procedure. In view of this, a microdose amount can be tailored to the specific indication of the substance delivery. When the device includes a plurality of chambers, each reservoir may deliver the same substance or different substances. A single reservoir having a combination of substances is also contemplated.

The devices may be configured for any route of delivery to the target tissue or retrieval from the target tissue. For example, they may be implanted via percutaneous, minimally invasive or open procedures into tissue, ingested, or topically applied. The devices may also be made to be flexible, bendable, expandable, or collapsible. In some variations, the devices are biodegradable or include one or more biodegradable portions. In other variations, the devices are nonbiodegradable.

The devices described here may be configured as a microchip. In some variations, the devices include a biopsy mechanism for retaining tissue upon retrieval. In other variations, the devices include an assay component capable of evaluating samples or the general behavior of a substance in vivo, and preferably in real time. In vitro methods may also be used to evaluate samples that are obtained, including samples withdrawn into a reservoir of a device, or a cell that has migrated into a vessel of the device. In further variations, the devices include one or more sensors capable of sensing one or more parameters of the target tissue. The devices may include a memory component to store parameter or assay data, which can be downloaded after retrieval, or be configured to communicate the data outside the body. In another variation, the devices may be configured to deliver an active agent in response to the data or sensed parameter. If desired, a control mechanism may be used to time delivery of an active agent(s) to the target tissue. The control mechanism may also be used to time delivery of substances from reservoirs of devices having a plurality of chambers.

The systems for delivering the devices may include one or more of the devices described above, or a combination of those devices. A deployment tool for delivering the device and/or a retrieval tool for removing the device may also be employed. In one variation, the system comprises an imaging component for visualizing the device within the target tissue. In another variation, the system includes an energy source for activating release of a substance from the device. The systems and devices of the present invention may be used to perform a diagnostic procedure, a therapeutic procedure, or both.

The kits described here may also have one or more devices, or a combination of devices. When multiple devices are employed, they may be configured to communicate with each other, such as via a base station or a hand held wireless communication device. Any number of deployment or retrieval tools may also be included. The kit devices may deliver the same substance or active agent or different substances or active agents. Likewise, they may be designed so that the devices delivery the same microdose or different microdoses of a substance. In some variations, the kits include one or more ports or other assemblies that may be removably secured to the devices for imaging tissue, delivering substances or active agents, or sampling tissue. For example, the port may be a catheter that is removably secured at one end of the device within the body, and the other end located outside the body.

BRIEF DESCRIPTION OF THE DRAWINGS

FIG. 5 illustrates a schematic view of an exemplary substance delivery device having advanceable tissue penetrating reservoirs.

FIG. 6a illustrates a cross-sectional view of an exemplary reservoir including lead screw and plunger substance delivery and multiple outlet ports.

FIG. 6b illustrates a cross-sectional view of the reservoir of FIG. 6a with the plunger having advanced to delivery the substance.

DETAILED DESCRIPTION

Figure 1:
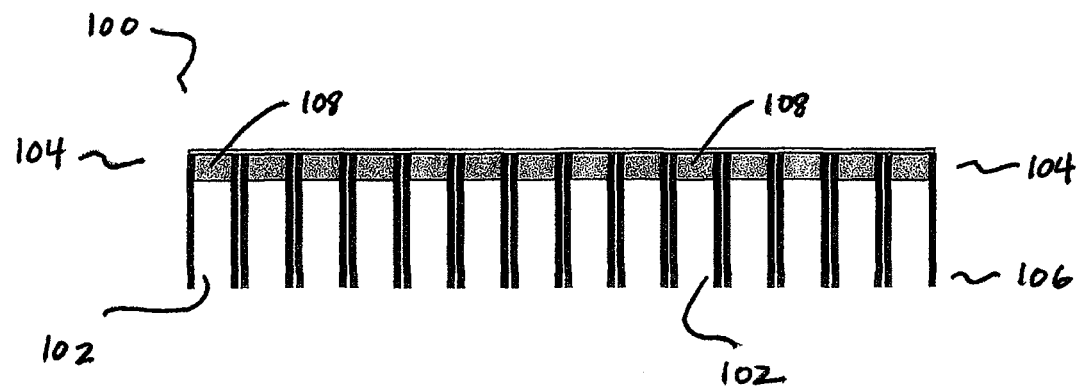
FIG. 1 depicts a side, cross-sectional view of an exemplary substance delivery device.

Described here are devices, systems, and kits for delivering substances to tissues. The devices may include one or more chambers and at least one reservoir within each chamber. The reservoir may locally deliver a microdose amount of a substance to a target tissue. The target tissue may be located anywhere in the patient's body such as locations including: liver, lung, kidney, prostate, ovary, spleen, lymph node, thyroid, pancreas, heart, skeletal muscle, intestine, larynx, esophagus and stomach. In a preferred embodiment, the target tissue is tumor tissue including but not limited to: adenoma, adenocarcinoma, squamous cell carcinoma, basal cell carcinoma, small cell carcinoma, large cell undifferentiated carcinoma, chondrosarcoma, fibrosarcoma. and combinations of these.

In some variations, the devices obtain or "biopsy" a sample of the target tissue at the time of implantation, upon removal or some time therebetween. By "sample" it is meant a tissue specimen obtained from the human body. In other variations, the devices are capable of obtaining in vivo data using an assay component coupled to the devices, and preferably configured to gather information in real time. The gathered assay information may be used to modify substance delivery and/or initiate or modify another medical event. In a preferred embodiment, the sample obtained is tumor cells and the assay provides information on tumor response, such as to manually, semi-automatically or automatically (i.e. closed loop) modify the delivery of one or more agents. The assay may be used to detect one or more of: a degree of agent permeation through the target tissue; detect a physiochemical effect of the agent on the target tissue; and detect a pharmacological effect of the agent on the tissue. In further variations, the devices may include a sensor for sensing one or more parameters of the target tissue after delivery of the substance. An agent may be delivered as a result of the response parameter or in response to the data obtained by the assay and/or sensor. The assay may be configured to provide various data such as data related to efficacy such as chemotherapeutic efficacy; activity such as tumor cell invasiveness; toxicity such as toxicity due to one or more agents being delivered or toxicity due to cell death; and combinations of these.

In yet further variations, the substance delivered by the devices is a position marker, such as a contrast agent. Image markers such as a radiolabel, a radio-opaque label, a fluorescent label, a colorimetric label, a dye, an enzymatic label, a GCMS tag, avidin, and/or biotin may be used. Here the devices are generally employed in conjunction with an imaging modality, such as x-ray, ultrasound, computed tomography (CT), magnetic resonance imaging (MRI), or nuclear imaging. The contrast agent may be locally delivered to obtain structural or functional information from the target tissue. The devices may also deliver a sensitizing agent, alone or in combination with a contrast agent. The sensitizing agent may increase the sensitivity of the tissue to radiation (either for imaging or treatment), or increase the contrastivity or resolution of the contrast agent within a tissue. The substance delivered may include controls, such as a negative control and a positive control often used in the diagnosis of a cancer. The substance delivered may include an efficacy indicator, such as an indicator of the efficacy of a cancer treatment such as chemotherapy. Efficacy indicators include but are not limited to: indicator dyes, indicators comprising nanoparticles or a nanostructure; and combinations of these.

The devices may be configured for any route of delivery. For example, the device may be implanted, ingested, or topically applied. Depending on the form taken, the devices will include suitable anchoring, fixation, or adhesive features, or coatings to aid delivery or prevent degradation or contamination. The substance delivered may include multiple agents, such as multiple agents contained in a single chamber or reservoir, or the agents may be stored and delivered singly, without any mixing prior to delivery.

I. Devices

The devices described here generally include one or more chambers. The chambers usually have a proximal end and a distal end. A reservoir may be included within each chamber. A support structure may also be coupled to the proximal end of the chambers. The chambers may be arranged in numerous geometries such as with the axes of the chambers relatively parallel, the distal ends of the chambers in a relatively single plane. In this configuration the chambers can be arranged in rectangular or circular arrays. The chambers may be equally spaced from one another or irregularly spaced. Alternatively, the chambers may be arranged in a three-dimensional pattern where the distal ends of the chambers lie in multiple planes. In this three-dimensional pattern the axes of the chambers may be relatively parallel or be skewed relative to one another The devices may be made from any material that does not interfere with delivery of the substance, assays performed, or data collection, if employed. The material may be a biodegradable or nonbiodegradable material, e.g., a polymer, a metal, etc., or combinations thereof. In some variations, the devices include an agent that prevents or reduces biofilm formation or inflammation or other foreign body reaction to the device once implanted. Such an agent may be incorporated within the material of the device itself, or coated on the device, or portions thereof. Other device modifications, including polymer treatments, may also be used to prevent such reactions.

The chamber may be of varying design, so long as its dimensions are suitable for the target tissue and allow delivery of the appropriate microdose of a substance. For example, the chamber may be formed to have a tubular, rectangular, square, etc., shape. When configured to have a length and a width, the chamber may be between about 1.0 mm to about 10 mm, between about 1.0 mm to about 5.0 mm, or between about 1.0 mm to about 3.0 mm in length. With respect to width, the chamber may be between about 0.1 mm to about 5.0 mm, between about 0.1 mm to about 3.0 mm, between about 0.1 mm to about 1.0 mm, or between about 0.1 mm to about 0.5 mm in width. Alternatively, the chamber may have a volume of between about 0.1 mm$^3$ to about 1.0 mm$^3$, between about 0.1 mm$^3$ to about 0.5 mm$^3$, or between about 0.1 mm$^3$ to about 0.3 mm$^3$. Other chamber dimensions may be used, e.g., to optimize device placement or to tailor the device for specific applications. For example, the width, length, and diameter of the chambers may be as small as 0.01 mm or larger than 10 mm. The chambers may also be configured to hold another component or device that would be capable of releasing a substance or active agent.

As mentioned above, the devices may include one or more chambers. Any number of chambers may be used. For example, from one to five, from one to 10, from one to 15, or from one to 20 or more chambers may be used. When a plurality of chambers are employed, the chambers may be directly adjacent to one another or have a space between them. In some variations, the chambers are configured to communicate with one another, e.g., so that contents of the chambers may be mixed.

The chambers may be removably attached to one another using an adhesive, or coupled to one another via a support structure at their proximal ends. For example, the support structure may include wells, depressions, or other connective elements to which the chambers may be friction fit, snap fit, or otherwise fixed to the support structure. The chambers may also be formed by molding, e.g., injection molding. If desired, the support structure may also include microfluidic channels.

The support structure may also be configured to have one or more areas of separation. For example, depending on such factors as the material used and number of chambers, the areas of separation may include perforations, a material of enhanced flexibility or lower durometer, hinges, joints, etc., which allow portions of the support structure to be separated. The chambers may be separated, e.g., when samples are to be run using different in vitro assays, or to group chambers by the substance delivered, particular response parameter sensed, or particular assay run in vivo. In some instances, the chambers may be formed in the support structure, by process such as etching, molding, or other machining, to form, e.g., a microchip.

The chambers and support structures may be made from any material or combination of materials. The material is generally biocompatible and provides the device with the desired residence time within the target tissue. In some instances a non-biocompatible material may be employed that is coated with another material to render the chambers and support structures biocompatible.

Any biodegradable polymer may be employed. For example, biodegradable polymers such as a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol)copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene)copolymer, or a blend or copolymer thereof, may be used. Biodegradable shape memory polymers, such as those commercialized by nmemoScience in Aachen, Germany, or those described in U.S. Pat. No. 5,189,110 or U.S. Pat. No. 5,139,832, may also be employed.

If a nonbiodegradable polymer is used in forming the chamber or support structure, suitable nonbiodegradable polymers include, but are not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

In some variations, the chambers or support structure may be made from a metal. Examples of suitable metals include, but are not limited to, cobalt, chromium, nickel, platinum, gold, silver, silicon metal, stainless steel, titanium, tantalum, and any of their alloys, e.g., nickel-titanium alloys, and combinations thereof. Biodegradable metals such as magnesium-based metals may also be used.

Each chamber will usually include a reservoir, but not necessarily. For example, some of the chambers may serve as a control, from which no substance is delivered. The reservoir may be of any geometry and of any type so long as it delivers the substance to the target tissue in the desired manner and at the desired microdose. For example, the reservoir may include the substance in a liquid, solution, gel, film, layer, or particulate form. In some variations, the reservoir comprises a polymer matrix that encapsulates the substance. In other variations, the reservoir includes a pump such as an osmotic pump, a microfluidic pump, or a microelectronic pump, or delivers the substance using such pumps operably coupled to the device. The reservoir may comprise a compressible bladder configured to deliver a substance while being compressed, such as a continually compressed bladder in fluid connection with a controllable valve. The reservoir may be pressurized, such as a gas pressurized reservoir, and the timing of the opening and closing of one or more valves causes the desired amount of substance to be delivered at the desired rate. The reservoir may include a cylinder and piston construction, such as a lead screw and plunger or a hydraulic or pneumatically driven piston.

Release of the substance from the reservoir may also be variously controlled. Control may be achieved through microcontroller or other form (e.g. mechanical) control of the various fluid driving mechanisms described above. Rates may be programmed into the pump prior to use, such as prior to implantation, or may be varied during use, such as an implanted delivery device that is in communication with an external controller. For devices wherein the substance includes multiple agents delivered independently, variable control is provided for each agent. Alternatively or additionally, the substance may be held within a matrix formed of a biodegradable material or a material which releases the incorporated substance by diffusion out of or degradation of the matrix, or by dissolution of the substance into surrounding interstitial fluid. When provided in a matrix, the substance may be homogeneously or heterogeneously distributed within the matrix.

Selection of the matrix may be dependent on the desired rate of release of the substance. Both biodegradable and nonbiodegradable matrices (release systems) can be used for delivery of the substances. Suitable release systems include, without limitation, polymers and polymeric matrices, non-polymeric matrices, or inorganic and organic excipients and diluents such as, but not limited to, calcium carbonate and sugar. The release systems may be natural or synthetic. In some variations, the release system may be selected based on the period over which release is desired, e.g., from about one day to about one week, from about one week to about one month, from about one month to about three months, or more. In other variations, the release duration may be as short as a few minutes to a few hours.

The reservoir may also be configured to release the substance continuously or non-continuously. In one variation, when non-continuous release is desired, the reservoir may be formed to provide one or more pulses of the substance to the target tissue. The pulsed substance may be delivered from one reservoir or multiple reservoirs. Incorporation of several layers of a release system and/or other materials into a single reservoir to achieve pulsatile delivery from a single reservoir is also contemplated. When continuous release is desired, the reservoir may include a release system that degrades, dissolves, or allows diffusion of the substance from it over a period of time. In some variations, a pump may be employed to achieve continuous or non-continuous delivery. Delivery may also be controlled by a remote signal.

The reservoir may be made from any material so long as it provides the reservoir with the desired release kinetics of the substance. In one variation, the reservoir may be formed from a biodegradable material such as a biodegradable polymer. Biodegradable polymers suitable for use with the reservoirs described here include, but are not limited to, polymers such as a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly(lactide-co-glycolide)/poly(ethylene glycol) copolymers; a poly(lactic acid)/poly(ethylene glycol) copolymers; a poly(glycolic acid)/poly(ethylene glycol) copolymers; a poly(lactic acid-co-glycolic acid)/poly(ethylene glycol) copolymers; a poly(caprolactone); poly(caprolactone)/poly(ethylene glycol) copolymers a poly(orthoester); a poly(phosphazene); a poly(hydroxybutyrate) or a copolymer including a poly(hydroxybutyrate); a poly(lactide-co-caprolactone); a polycarbonate; a polyesteramide; a polyanhidride; a poly(dioxanone); a poly(alkylene alkylate); a copolymer of polyethylene glycol and a poly-orthoester; a biodegradable polyurethane; a poly(amino acid); a polyetherester; a polyacetal; a polycyanoacrylate; a poly(oxyethylene)/poly(oxypropylene)copolymer, or a blend or copolymer thereof.

If a nonbiodegradable polymer is used in forming the reservoir, suitable nonbiodegradable polymers include, but are not limited to, poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof. In some instances the reservoir is made from a nonbiodegradable polymer that is porous to allow absorption and/or diffusion of the substance.

In other variations, the reservoir includes natural polymers. Representative natural polymers that may be employed include, but are not limited to, proteins, such as zein, modified zein, casein, chitin, gelatin, gluten, serum albumin, or collagen; and polysaccharides, such as cellulose, dextrans, and polyhyaluronic acid. Hydrogel or sol-gel mixtures of polysaccharides are may also be employed. The reservoir may also be filled with a porous polymer that provides controlled diffusion of the substance.

The reservoir may locally deliver any substance to the target tissue. The substance may be any compound, molecule, drug, prodrug, protein, peptide, gene therapy preparation, cell, diagnostic agent, contrast or imaging agent, etc., or combinations thereof. Such substances may be in bound or free form, liquid or solid, colloid or other suspension, solution, particles, including nanoparticles, or may be in the form of a gas or other fluid. For example, the substance may be a small molecule, DNA, RNA, polysaccharide, enzyme, or radioactive compound. The substance may be a candidate compound being evaluated for treatment of a medical condition or a substance for use in locally treating a medical condition (e.g., a commercially available drug). As previously mentioned, the substance may also be a contrast or imaging agent for use during a structural or functional imaging procedure.

When the substance is being evaluated as a candidate compound, it may be evaluated for the local treatment of various medical conditions (including the local cure of various medical conditions). For example, it may be evaluated to treat autoimmune conditions, cancer, cardiac conditions, endocrine conditions, dermatologic conditions, gastrointestinal conditions, genitourinary conditions, gynecologic, hematologic conditions, infectious conditions, inflammatory conditions, ischemic conditions, neurologic conditions, obstetric conditions, orthopedic conditions, proliferative conditions, pulmonary conditions, renal conditions, and vascular conditions, including cerebrovascular and peripheral vascular conditions.

In view of the above, exemplary categories of substances/candidate compounds that may be locally delivered to target tissues and evaluated, include without limitation, anti-inflammatory substances, antiproliferative substances, and chemotherapeutic/antineoplastic substances. Examples of anti-infective substances include, but are not limited to, antibacterial agents, antifungal agents, antiparasitic agents, antiviral agents, and antiseptics. Examples of anti-inflammatory substances include without limitation, steroidal and nonsteroidal anti-inflammatory agents. In addition to that listed above, these substances/candidate compounds may be polypeptides, polynucleotides, including antisense oligonucleotides, and naturally occurring or synthetic small molecule compounds.

In one variation, the substances delivered to the target tissue are naturally occurring or synthetic small molecule compounds having a molecular weight of more than about 50 and less than about 2,500 daltons. The substances may include functional groups necessary for structural interaction with proteins, particularly hydrogen bonding, and may include at least an amine, carbonyl, hydroxyl or carboxyl group. The substances may also comprise cyclical carbon or heterocyclic structures and/or aromatic or polyaromatic structures substituted with one or more of the above functional groups. In some variations, the substances may be saccharides, fatty acids, steroids, purines, pyrimidines, derivatives, structural analogs, or combinations thereof.

When the substance is a protein, it may be a human protein or a homolog or a protein (or fragment thereof) from another species, i.e., another animal species, e.g., rodents, such as mice and rats; domestic animals such as horses, cows, dogs, or cats; and primates, e.g., monkeys, or baboons. By "homolog" it is meant a protein having at least about 35%, usually at least about 40% and more usually at least about 60% amino acid sequence identity to the corresponding human protein (sequence identity may be measured by the BLAST Compare Two Sequences program available on the NCBI website using default settings).

In another variation, the substance delivered to the target tissue site is a polynucleotide or nucleic acid. The nucleic acid may be coding sequences, e.g., genes, gene fragments etc., which may be present in expression vectors, where such vectors generally have convenient restriction sites located near the promoter sequence to provide for the insertion of nucleic acid sequences. A transcription cassette may be prepared that includes a transcription initiation region, the target gene or fragment thereof, and a transcriptional termination region. The transcription cassette may be introduced into a variety of vectors, e.g., plasmid; retrovirus, e.g., lentivirus; adenovirus; and the like, where the vectors are able to transiently or stably be maintained in the cells for the desired time period.

In other variations, the substance is an antisense oligonucleotide, particularly a synthetic antisense oligonucleotide having chemical modifications from native nucleic acids, or nucleic acid constructs that express such anti-sense molecules as RNA. The antisense sequence may be complementary to the mRNA of a targeted gene, and may inhibit expression of the targeted gene products. Antisense molecules inhibit gene expression through various mechanisms, e.g., by reducing the amount of mRNA available for translation, through activation of RNAse H, or steric hindrance. One or a combination of antisense molecules may be used as a substance. When a combination is used, the substance may comprise multiple different sequences.

Alternatively, the substance may be double-stranded RNA molecules. RNAi, otherwise known as double-stranded RNA interference (dsRNAi) or small interfering RNA (siRNA), has been extensively documented in the nematode C. elegans (Fire, A., et al, Nature, 391, 806-811, 1998). The RNAi molecules may be small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By "oligoribonucleotide" it is generally meant a ribonucleic acid that does not exceed about 100 nt in length, and usually does not exceed about 75 nt length. However, in some instances, the length may be less than about 70 nt. Where the RNA agent is a duplex structure of two distinct ribonucleic acids hybridized to each other, e.g., an siRNA, the length of the duplex structure may range from about 15 to about 30 bp or from about 15 to about 29 bp. Where the RNA agent is a duplex structure of a single ribonucleic acid that is present in a hairpin formation, i.e., a shRNA, the length of the hybridized portion of the hairpin may be the same as that provided above for the siRNA type of agent or longer by 4-8 nucleotides. In this instance, the weight of the RNAi agents may range from about 5,000 daltons to about 35,000 daltons.

Figure 2:
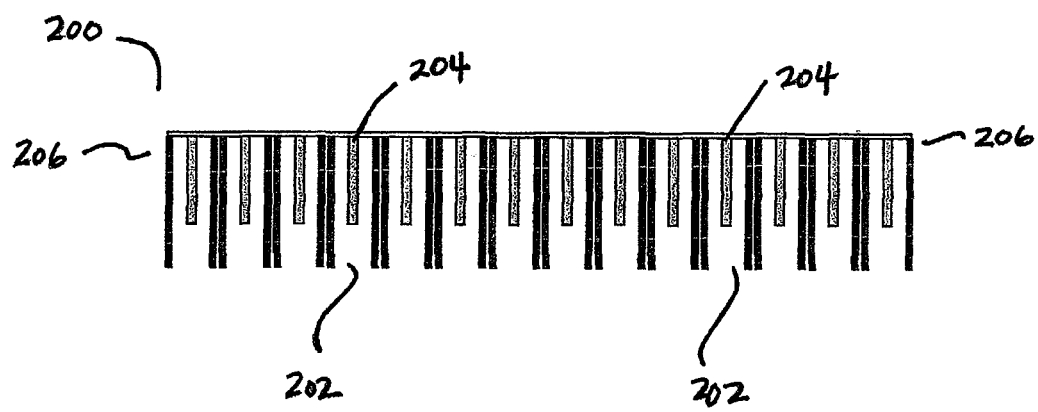
FIG. 2 shows a side, cross-sectional view of an exemplary substance delivery device having a reservoir configured for implantation into tissue.

Referring to the figures, an exemplary device is shown in FIG. 1. In this variation, substance delivery device (100) includes a plurality of chambers (102) having a proximal end (104) and a distal end (106). A reservoir (108) lies within each chamber (102). Although the reservoir (108) is located at the proximal end (104) of the chamber (102), other configurations are contemplated. For example, as illustrated in FIG. 2, the chambers (202) of device (200) include elongate reservoirs (204) that extend from the proximal end (206) of the chambers (202). The chambers may be configured to penetrate tissue, e.g., by employing a sharp or needle-like distal end. The reservoirs or portions thereof, may also be similarly configured as a penetrating member, with a sharpened distal end, in a near-linear and/or curved geometry. These penetrating members may be configured to be deployed during use, such as being advanced after the substance delivery device has been attached to the patient's skin or after it has been implanted within the patient. Alternatively or additionally, the penetrating members may be configured to be advanced or retracted at any time, such as prior to use, just prior to explantation, or after explantation. The advancement or retraction of the penetrating members may be image guided, such as real-time guidance or guidance based on an image taken previously. The penetrating members may be hollow or include one or more lumens, and include stiffening means to aid in advancement or retraction, such as to prevent buckling during advancement. In a preferred embodiment, the stiffening means comprises a dissolvable biocompatible substance, not shown but preferably an inert compound such as salt which is dissolved shortly after the device is implanted. Alternatively, a removable mandrel may be included within the penetrating member to provide stiffness.

The penetrating members may be driven by one or more linear actuators, such as hydraulic or pneumatic pistons, magnetic drives, lead screw drives, thermal expansion or contraction assemblies, and other linear actuating assemblies configured to advance or retract the penetrating members in a continuous movement and/or in discrete steps. These penetrating members may be advanced or retracted on demand by a user such as a clinician or the patient, or may automatically advance or retract. The substance delivery device may include a sensor, such as a sensor on or near the penetrating member, to detect and/or measure the movement of the penetrating member. The distal ends of the three or more penetrating members may lie in a single plane or multiple planes. In a preferred method, the distal ends of the penetrating members reside, with or without deployment, in an area or volume with a substantially constant width, thickness or diameter, such as in an area defined by the long axis of a tumor. After delivery of one or more agents, this defined area or volume is excised and analyzed. A comparison of efficacy or other tissue response is performed based on the independent delivery of two or more agents to the defined area. Tissue excision is performed at a time related to efficacy or other agent-related time parameter. In a preferred embodiment, excision is performed two to seven days after initiation of agent delivery. In another preferred embodiment, excision is performed one week to one year after initiation of agent delivery.

The devices described here may also include one or more sensors for sensing a response parameter in vivo. Any type of sensor may be employed. For example, chemical sensors, mechanical sensors, optical sensors, radiation sensors, temperature sensors, or a combination of these sensors may be used. Nanosensors may be employed. The response parameter may be any parameter capable of being sensed or measured by the sensor in the target tissue, and which relates to an effect or response of the target tissue to the substance. The response parameters may include without limitation, levels of metabolites or precursors; levels of glucose, oxygen, or other nutrients; cytokine levels; pH; or osmolality. In some variations, the response parameters are structural in nature, and are obtained through visualization, e.g., via an optical sensor. For example, visualization of cellular or histological/histopathological changes may be obtained. When devices that are removed take samples from the target tissue, further in vitro characterization of the samples may occur. A docking station or other device may be used to collect the tissue samples or perform various assays in further characterizing the samples.

The devices may also be configured to locally deliver an active agent in response to the response parameter. Exemplary active agents that may be locally delivered include, but are not limited to, anti-infective agents, anti-inflammatory agents, anti-proliferative agents, and chemotherapeutic/antineoplastic agents. Examples of anti-infective agents include, but are not limited to, antibacterial agents, antifungal agents, antiparasitic agents, antiviral agents, and antiseptics. Examples of anti-inflammatory agents include without limitation, steroidal and nonsteroidal anti-inflammatory agents.

Examples of antibacterial agents that may be locally delivered include, but are not limited to, aminoglycosides, amphenicols, ansamycins, β-lactams, lincosamides, macrolides, nitrofurans, quinolones, sulfonamides, sulfones, tetracyclines, vancomycin, and any of their derivatives, or combinations thereof. In one variation, β-lactams are the active agents.

The β-lactams that may be used include, but are not limited to, carbacephems, carbapenems, cephalosporins, cephamycins, monobactams, oxacephems, penicillins, and any of their derivatives. In one variation, penicillins (and their corresponding salts) are the active agents.

The penicillins that may be locally delivered by the devices described here include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. Penicillins combined with clavulanic acid such as Augmenting (amoxicillin and clavulanic acid) may also be used.

Examples of antifungal agents suitable for local delivery include, but are not limited to, allylamines, imidazoles, polyenes, thiocarbamates, triazoles, and any of their derivatives. In one variation, imidazoles are the preferred antifungal agents. Antiparasitic agents that may be employed include such agents as atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for local delivery include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-1-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-1-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N—,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Antiseptic agents that may be locally delivered include, but are not limited to, alcohol, chlorhexidrine, iodine, triclosan, hexachlorophene, and silver-based agents (e.g., silver chloride, silver oxide, silver nanoparticles).

The devices may also locally deliver an anti-inflammatory agent such as a steroidal anti-inflammatory agent (corticosteroid). Exemplary steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

In some variations, a nonsteroidal anti-inflammatory agent is locally delivered. For example, nonsteroidal anti-inflammatory agents that may be used include, but are not limited to, COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide).

In other variations, chemotherapeutic/antineoplastic agents are locally delivered. For example, chemotherapeutic/antineoplastic agents that may be delivered by the devices described here include, but are not limited to, antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12), biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, analogs/congeners, derivatives of such compounds, and combinations thereof.

In some variations, a closed feedback loop is generated that is dependent on the sensed response parameter. For example, when a device is used to locally deliver a chemotherapeutic agent to treat a malignant tumor, or to determine the optimal agent or agent combination to use for chemotherapy, decreased or increased levels of the chemotherapeutic agent may be released from the device based on the amount of tumor cell apoptosis that is sensed. Similarly, when a device is used to locally deliver an anti-inflammatory agent to treat inflammation, decreased or increased levels of the anti-inflammatory agent may be released from the device based on the level of cytokines sensed in the target tissue. In other variations, the sensed response parameter is linked to systemic administration, e.g., intravenous administration, of an active agent.

The devices described here may also include elements that aid its identification or detection by imaging modalities. With respect to detection, the devices may have a radiopaque or fluorescent marker. A radiofrequency tag may be used for identification purposes. In some variations, the devices include a visual indicator for indicating upon explants whether a particular effect or response has occurred in the target tissue. The visual indicator may be a color change of all or a portion of the device.

Figure 3:
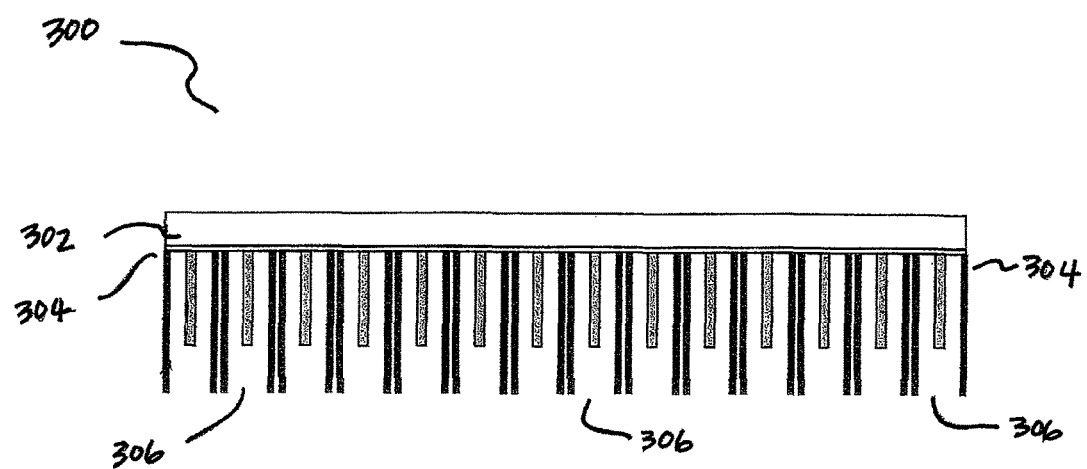
FIG. 3 shows a side, cross-sectional view of an exemplary substance delivery device having an in vivo assay component.

The substance delivery devices so far described generally include one or more chambers and a reservoir within each chamber. The reservoirs may contain a substance for delivery to a target tissue. Taking this general structure, devices having a particular functionality or application, as further elaborated below, may be designed. For example, the substance delivery devices may be constructed to include microchips, biopsy mechanisms, or various assay components. Devices with biopsy mechanisms may be suitable for implantation, while devices including microchips or assay components may be suitable for either implantation, ingestion, or topical application. As shown in FIG. 3, the substance delivery device (300) includes a microchip (302) coupled to the proximal end (304) of chambers (306). When an assay component is employed, it may also be coupled to the proximal end of the chambers.

Microchip Devices

In one variation, the substance delivery device includes a microchip. The microchip may be used to locally deliver the substance to a target tissue, control substance delivery, etc. For example, each of the reservoirs of a microchip may be loaded with different substances and/or different microdose amounts of the substances, which can be released independently. Release from a microchip device may be controlled by a preprogrammed microprocessor, remote control, or by sensors.

Instead of chambers, the microchip device may include a plurality of reservoirs that are etched into or otherwise formed in a biocompatible substrate, which are filled with a substance(s). Release of the substance from each reservoir may be separately controlled, for example, by a barrier membrane or other controllable member that controllably effects release of the substance from the reservoir. Reservoirs may be filled with different drugs, and the reservoirs can be capped with materials that either degrade or allow the drugs to diffuse passively out of the reservoir over time. The capping material may be structured such that upon exposure to an energy source, it erodes quickly, changes permeability or otherwise responds to a signal to release the substance. The sites and times of this substance release may then be controlled by a remote controller, by an integrally implanted programmed microprocessor, by an implanted but externally programmable unit, or other effective arrangement.

The microchip devices and other devices of the present invention may also include a pump such as a microfluidic pump, an osmotic pump, or a microelectronic pump. In general, the pump assembly, or multiple pump assemblies, will deliver a carrier fluid to a fluid outlet, and a fluid delivery pathway will extend from the outlet past a reservoir to a distal ported outlet, which is implanted at a target tissue site. In this configuration, the reservoir, positioned in or in communication with the fluid delivery pathway, releases a substance into the carrier fluid, which is delivered by the pump assembly at a rate effective to establish a local pressure gradient in the region of the ported outlet at the target tissue site, so that the substance is delivered into the tissue at the target tissue site. The carrier may be, e.g., a biologically inert or inactive fluid such as physiologic saline, or it may be an endogenous body fluid. In an alternative embodiment, multiple pump assemblies deliver carrier fluid to one or more fluid conduits and fluid outlets, such as to deliver different types of carrier fluids for combination with different agents released by different reservoirs into the fluid conduits or outlets. Each pump assembly is preferably independently controllable, to allow independent control of each agent's delivery rates, time of infusion and amount of infusion.

When the reservoir is a pressurized assembly, such as a pressure-driven bellows, the pump assembly may work by simply providing one or more valves, restrictors or other elements that regulate the time and/or the rate at which the substance is allowed to pass from the reservoir. Alternatively, the pump may be an electrically powered assembly, having a power source and a controller.

The precise pump structure may include any suitable structure as known in the art, either with an electromechanically-actuated peristaltic or displacement pumping mechanism, or with a pressurized reservoir or osmotically-driven source connected to a control valve or restrictor assembly to regulate the provision of fluid into the fluid delivery path. In either case, whether powered by pressure or electromechanically, the pump assembly will be configured to produce an accurate and sustainable flow of a total volume of fluid at a suitable flow rate.

The control circuitry may consist of a timer, a demultiplexer, a microprocessor, and an input source, for example, a memory source, a signal receiver, or a biosensor. The timer and demultiplexer circuitry may be designed and incorporated directly onto the surface of the microchip during electrode fabrication. The microprocessor will generally be of small size, have a low power requirement, and have the ability to translate the output from memory sources, signal receivers, or biosensors into an address for the direction of power through the demultiplexer to a specific reservoir on the substance delivery device. Selection of a source of input to the microprocessor such as memory sources, signal receivers, or biosensors depends on the particular application of the delivery device and whether the device operation is preprogrammed, controlled by remote means, or controlled by feedback from its environment.

The criteria for selection of a power source for a microchip may be small size, sufficient power capacity, ability to be integrated into the control circuitry, the ability to be recharged, and the length of time before recharging is necessary. Several lithium-based, rechargeable microbatteries have been described by S. D. Jones and J. R. Akridge, "Development and performance of a rechargeable thin-film solid-state microbattery", Journal of Power Sources, 54:63 67 (1995); and J. B. Bates et al., "New amorphous thin-film lithium electrolyte and rechargeable microbattery", IEEE 35$^{th}$ International Power Sources Symposium, 337 39 (1992). These batteries are typically only about 10 μm thick and occupy about 1 cm$^2$ of area. One or more of these batteries may be incorporated directly onto the microchip device.

Referring now to FIG. 5, a substance delivery device of the present invention is illustrated. Device 500 includes housing 505, which surrounds an electronic controller, microcontroller 501 which is electrically attached to wireless transceiver 503 and a power supply, battery 502. Device 500 is configured for placement near target tissue, such as via adhesive attachment of a portion of housing 505 to the patient's skin, or via implantation within the patient such as by using suture and suture loops 504 to fixate housing 505 to tissue proximate the target tissue. Device 500 includes a series of chambers, including chamber 520a. Each chamber includes and slidingly receives a movable reservoir, such as reservoirs 550a, 500b, 550c and 550d. Each reservoir is configured to contain one or more agents, as are described and listed in detail throughout the application, and deliver these one or more agents to the target tissue. The target tissue can be any location in the patient's body, such as organ tissue and tumor tissue. In a preferred method, the target tissue includes both tumor and healthy tissue, such as when substance is delivered into, and/or tests are performed on, both tumor and healthy tissue, such as to include a control A typical embodiment of a reservoir is described in reference to FIGS. 6a and 6b below. Chamber 520a and reservoir 550a are sized and constructed such as to form a seal such that gas pressure created within chamber 520a causes reservoir 550a to advance. A sealing component, not shown but preferable an O-ring, can be included between reservoir 550a and chamber 520a to form the seal. Reservoir 550a is attached to microcontroller 501 via a spiral wire 551a. Spiral wire 551a is configured to accommodate the advancement of reservoir 550a, such as the advancement of reservoir 550b and 550c shown in FIG. 5. Reservoir 550a includes at its distal end tip 555a, preferably of an anti-coring needle configuration with a lumen configured to deliver the one or more agents contained in reservoir 550a, such as through a hole in the distal end of the tip or from side holes located along the side of the tip, not shown but described in detail in reference to FIGS. 6a and 6b below. Cylinder 521a, contained within chamber 520a, is preferably a gas delivering element such as a gas generator assembly, or a compressed gas vessel controlled by one or more valves.

Cylinder 521a is electrically connected to microcontroller 521 such that a precise amount of gas can be released by cylinder 521 to specifically advance reservoir 550a and tip 555a into the target tissue. One or more sensors, not shown but preferably an optical or magnetic sensor, can be placed to detect and/or quantify the motion of cylinder 550a and provide closed loop motion information to microcontroller 501. While the chambers and reservoirs are shown in a linear configuration, numerous two and three dimensional arrangements of chambers can be employed, such as a ten by ten square array of chambers and reservoirs. While each reservoir of FIG. 5 is advanced by increasing the pressure in the associated chamber, other linear actuators can be employed. In a preferred embodiment, a lead screw is driven by a rotational motor, both not shown, wherein the reservoir is rotationally attached to the lead screw and the reservoir can be advanced or retracted by associated forward and reverse rotations of the motor. Advancement and retraction of the reservoir can be performed prior to, during, and/or after skin attachment or implantation of the substance delivery device of the present invention. The fluid delivery and other moving components of the substance delivery devices of the present invention may be constructed using semiconductor-like machinery, such as with microelectromechanical system (MEMS) construction. MEMS assemblies and components include motors, valves, actuators and other electromechanical components that can be produced at extremely small dimensions, such as the dimensions that are preferred for the components and devices of the present invention.

Referring now to FIGS. 6a and 6b, a preferred embodiment of a reservoir of the present invention is illustrated. Reservoir 550 includes one or more attached wires, not shown but preferably for connection to one or more electronic circuits, such as microcontroller 501 of FIG. 5. Motor 552, a rotational motor such as a stepper motor including one or more gear reducing assemblies, is connected to lead screw 554 such that rotation of motor 552 causes lead screw 554 to rotate. Motor 552 may include one or more rotational sensors such as optical encoders or Hall effect motion sensors. Plunger 553 is rotatingly attached to threads of lead screw 554, not shown but of a constant or otherwise thread pitch such that the linear advancement of plunger 553 can be calculated based on known angle of rotation of motor 552. Plunger 553 forms a seal against the walls 558 of reservoir 550 such that linear advancement of plunger 553 causes a specific amount of agent 10 to be delivered to target tissue. Plunger 553 may have an eccentric cross-section, or include one or more notches that mate with walls 558 such as to prevent rotation of plunger 553. The distal end of reservoir 550 includes a sharpened distal tip configured to penetrate tissue, and outlet ports 557a, 557b and 557c, all fluidly connected to the agent 10 contained within the walls 558 of reservoir 550. Reservoir 550 may include varied placement of one or more fluid delivery outlet ports, and the outlet ports may have different geometries and/or cross-sectional areas. For example, a first outlet port distal to a second outlet port may have a bigger cross-sectional area such as to cause the same amount of agent to be delivered through each outlet port. The outlet ports may be equally spaced and/or the ports may be oriented in a spiral pattern.

Retraction of plunger 553 is caused by rotation of the motor in the opposite direction to that causing advancement. Retraction of plunger 553 can be used to extract fluid from the patient into reservoir 550. Such extraction may occur when reservoir 550 is void of agent 10, such as after plunger 553 has been fully advanced or when plunger 550 is provided in the fully advanced position (i.e. no agent included). The extraction can be used to withdraw one or more body fluids including but not limited to: blood; lymphatic fluid; urine; semen; cerebral spinal fluid; interstitial fluid; and combinations of these.

Reservoir 550 includes a first sensor, volume detector 523 which is integrated into reservoir 550 behind plunger 553, and attaches to electronic circuitry, not shown but preferably similar to microcontroller 501 of FIG. 5. Advancement or retraction of plunger 553 can be confirmed and/or quantified by the change in volume behind plunger 553. In a preferred embodiment, volume detector 523 includes circuitry to produce, or otherwise is provided (e.g. from the microcontroller) a range of frequencies which are converted to sound by a speaker of volume detector 523. A microphone of volume detector 523 records the sounds created within the confined space or cavity around volume detector 523 such that a resonant frequency can be detected. This resonant frequency, the Helmholtz resonance, is proportional to the volume of the confined space.

Reservoir 550 further includes, at or near its distal tip, sensor 556 configured to be advanced into the target tissue as reservoir 550 penetrates the target tissue, such as been described above in reference to FIG. 5. Sensor 556 may be configured to detect motion, such as an optical detector configured to detect and/or quantify the motion of reservoir 550. Alternatively or additionally, sensor 556 may be a sensor such as a strain gauge, an accelerometer, a temperature sensor, a pH sensor, a chemical sensor, a mechanical sensor, a radiation sensor and/or a physiologic sensor. Numerous physiologic sensors can be employed such as those configured to assess one or more cell activities.

Biopsy Devices

In another variation, the substance delivery device may be configured to obtain a sample upon its removal from the target tissue. The sample may be cells or portions of tissue from any organ (e.g., liver) or target tissue (e.g., a cancer or tumor) at the target site. The sample may also be a body fluid sample such as serum, blood, blood cells (e.g., white cells), plasma, sputum, urine, peritoneal fluid, pleural fluid, cerebrospinal fluid, or lymphatic fluid. As mentioned above, the samples may be obtained using a sampling port.

Figure 4A:
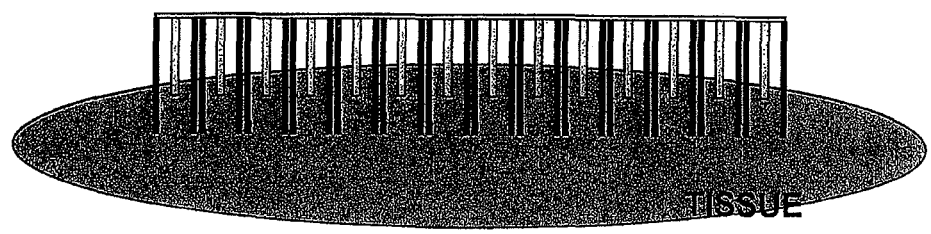
FIGS. 4A-4C illustrates an exemplary method of obtaining a tissue sample using an exemplary biopsy device.
Figure 4B:
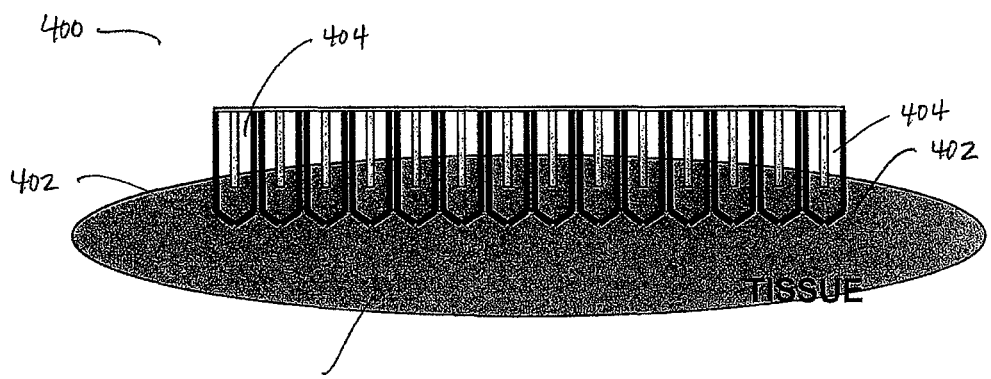
Figure 4C:
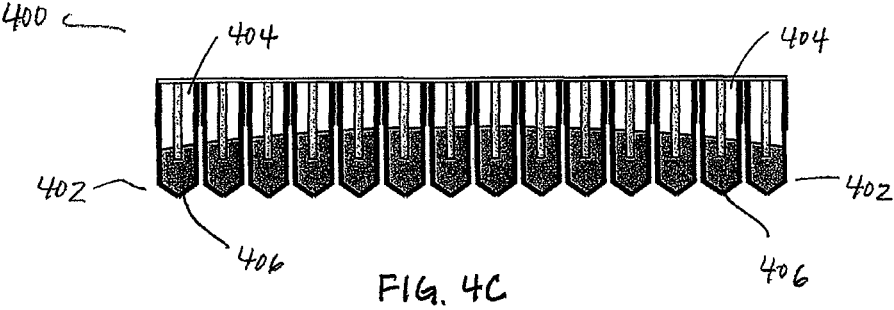

The devices may obtain samples using any type of biopsy mechanism. In one variation, as shown in FIG. 4B, device (400) has a biopsy mechanism that causes the distal end (402) of the chambers (404) to move from an open position (FIG. 4A) to a closed position (FIG. 4B). Such a biopsy mechanism may include hinges, springs, shape memory elements, wires, or combinations thereof. The biopsy mechanism may be activated by an external controller, pressure changes, temperature changes, etc., or be automatically activated after a predetermined period of time. Furthermore, the biopsy mechanism may include a chamber having a cutting edge at its distal end.

Upon closure of the distal ends (402) of the chambers (404), a sample, e.g., tissue (406) may be retained within the chambers (404). Tissue (406) may then be subjected to various in vitro assays for evaluation of response parameters. Suitable in vitro assays are well known in the art. For example, binding assays, spectrophotometry, gel electrophoresis, chromatography, etc., may be performed using the samples.

Assay Devices

In other variations, the devices include an assay component (see, e.g., FIG. 3, element 302) for evaluating a sample obtained from the target tissue in vivo. The assay may incorporate one or more sensors, as previously described, or other elements capable of analyzing the sample. For example, the assay may include elements capable of detecting levels of antibodies, serum proteins, enzymes, viral or bacterial proteins, cholesterol, glucose, polysaccharides, nucleic acids, metabolites, cytokines, tumor antigens or cancer markers, and apoptosis. In some variations, the assay devices are configured to deliver an active agent in response to the data obtained from the assay. The active agents that may be delivered are the same as those previously described above. However, specific examples of what the assay component may detect and analyze, and the corresponding active agents that may delivered in response to the assay data is further provided below.

In some variations, the assay devices are used to monitor or locally treat various types of tumors and cancers. Here the assay component may be configured to detect and analyze genes or their products which are over-expressed or over-active in cells undergoing unwanted proliferation. For example, the assay device may be implanted into a tumor or a tissue suspected of containing a tumor such as a cavity or space left behind following a biopsy procedure. If the assay component detects increased concentrations of such biological analytes or mutated over-active forms of such analytes (both disease markers), then the assay device may be configured to release an active agent such as a cytotoxic agent. Similarly, a cytotoxic agent may be released in response to analytes corresponding to neointimal proliferation, among other pathologic conditions.

In other variations, the biological analytes are tumor specific antigens, which may be expressed on the surface of or released from cancer cells, for example the tumor specific antigen MUC-1. Here the assay device may be configured to release a cytotoxic agent in response to the detection of MUC-1.

In yet other variations, the assay component detects the presence of receptor tyrosine kinases (RTKs) in the sample. These receptors are frequently present in common human cancers such as breast cancer; squamous cell cancer of the lung; bladder cancer; esophageal cancer; gastrointestinal cancer such as colon, rectal or stomach cancer; leukemia;

ovarian cancer; bronchial cancer; and pancreatic cancer. Accordingly, detection of abnormally high levels of RTK expression or signaling activity through nucleic acid detection or by protein activity can constitute a disease marker and can warrant the release of RTK inhibitors or cytotoxic agents as active agents.

In further variations, the assay component is configured to detect analytes that may be indicative of inflammation, such as TNF-alpha, IL-1, IL-8, IL-2, IL-3, IL-4, GM-CSF, INF-gamma, MIF, and TNF-beta. The detection of abnormally high concentrations of such analytes may trigger the localized release of anti-inflammatory drugs or antibodies as active agents.

In yet further variations, the assay component is configured to detect analytes that may be indicative of infection by a microorganism. Here the analytes may include viral or bacterial proteins or nucleic acids or fragments thereof. For example, detection of analytes such as bacterial toxins including exotoxins and enterotoxins as well as TSST-1, or other bacterial superantigen, or botulinum toxin, diphtheria toxin, anthrax protective antigen, anthrax edema factor, and anthrax lethal factor, etc., as well as viral proteins such as influenza hemagglutinin or neuramimidase, may indicate an infection and might trigger localized release of an anti-infective agent or a toxin-specific antibody as active agents.

In another variation, the assay component is configured to detect abnormal cellular proliferation, and coordinate localized release of an active agent that has an anti-proliferative effect. For example, sirolimus (rapamycin) or paclitaxel, which are effective in inhibiting smooth muscle cell proliferation during neointimal hyperplasia, may be released. In yet another variation, 5-FU chemotherapy is locally released from the assay device in response to detected analytes associated with abnormal cellular proliferation. 5-FU-based chemotherapy may comprise administration of 5-FU, its derivatives, alone or with other chemotherapeutics, such as leucovorin or with a DPD inhibitor such as uracil, 5-ethynyluracil, bromovinyluracil, thymine, benzyloxybenzyluracil (BBU) or 5-chloro-2,4-dihydroxypyridine.

Alternatively, genotoxic agents such as DNA alkylating agents and DNA intercalating agents may be delivered. For example, psoralens, antineoplastic antibiotics, which include, but are not limited to, amsacrine; actinomycin A, C, D (alternatively known as dactinomycin) or F (alternatively KS4); azaserine; bleomycin; caminomycin (carubicin); daunomycin (daunorubicin), or 14-hydroxydaunomycin (adriamycin or doxorubicin); mitomycin A, B or C; mitoxantrone; plicamycin (mithramycin); and the like, may be delivered. Another general class of genotoxic agents that may be locally delivered, and which alkylate DNA, are those that include the haloethylnitrosoureas or chloroethylnitrosoureas. Representative members of this class include, but are not limited to, carmustine, chlorozotocin, fotemustine, lomustine, nimustine, ranimustine and streptozotocin.

In some instances, platinum coordination compounds such as cisplatin or oxaliplatin may be delivered alone or in combination in response to analytes associated with testicular, endometrial, cervical, gastric, squamous cell, adrenocortical, and small cell lung carcinomas, as well as medulloblastomas and neuroblastomas.

Yet another general class of genotoxic agents that may be locally delivered in response to a detected tumor analyte includes the sulfur and nitrogen mustards. These compounds damage DNA primarily by forming covalent adducts at the N7 atom of guanine. Representative members of this broad class include chlorambucil, cyclophosphamide, ifosfamide, melphalan, mechloroethamine, novembicin, and trofosfamide. Oligonucleotides or analogs thereof that interact covalently or noncovalently with specific sequences in the genome of selected cells may also be used as genotoxic agents, if it is desired to select one or more predefined genomic targets as the locus of a genomic lesion.

In some variations, the assay component is configured to detect an analyte indicative of a microbial pathogen. In response, the device may be configured to locally release an active agent that has an antimicrobial effect. For example, an antibiotic or antiviral agent may be released.

In other variations, the assay component is configured to detect an analyte indicative of hyperglycemia and the assay device, in response, designed to locally release an active agent suitable to reduce serum glucose levels. For example, when excessively high levels of glucose are detected by the assay component, the assay device may respond by releasing a sufficient amount of insulin to normalize the blood glucose level.

Patch Devices

The substance delivery devices may also be formed as a patch. The patch may be useful when topical application of the device to the skin is desired. In this variation, the reservoir containing the substance may be a layer underlying an upper backing layer. The patch may contain a single reservoir, or it may contain multiple reservoirs. When multiple reservoirs are employed, they may include the same substance or different substances, or each reservoir may include a combination of substances. The patches may also be configured to include a component that modifies delivery of a substance therefrom. For example, a rate-limiting membrane may be placed between the reservoirs to modify release of the substance. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

In some variations, the reservoirs may comprise a polymeric matrix of a pharmaceutically acceptable adhesive material that serves to affix the patch to the skin. For example, the adhesive material may be a pressure-sensitive adhesive (PSA) including, but not limited to, polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene).

The backing layer may function as the primary structural element of the patch and may provide the device with flexibility and in certain variations, occlusivity. The backing may be comprised of a flexible elastomeric material that serves as a protective covering to prevent loss of the substance via transmission through the upper surface of the patch, and may impart a degree of occlusivity to the patch, such that the area of the body surface covered by the patch becomes hydrated during use. The material used for the backing layer may permit the patch to follow the contours of the skin and be worn comfortably on areas of skin such as at joints or other points of flexure that are normally subjected to mechanical strain, with little or no likelihood of the patch disengaging from the skin due to differences in the flexibility or resiliency of the skin and the patch. The materials used as the backing layer may be either occlusive or permeable, as noted above, and may be made from synthetic polymers (e.g., polyester, polyethylene, polypropylene, polyurethane, polyvinyl chloride, and polyether amide), natural polymers (e.g., cellulosic materials), or macroporous woven and non-woven materials. In other variations, a microchip and/or assay component may be provided in lieu of a backing layer. Alternatively or additionally, the adhesive may be applied to the skin-contacting surface of the patch in discrete areas, such as to allow certain portion of the patient's skin under the patch to remain unattached (i.e. the areas void of adhesive). This discontinuous configuration may avoid undesired cosmesis and other skin effects, as well as accommodate skin motion thus avoiding undesired detachment of the patch. In an alternative embodiment, the patch is flexible, or includes one or more hinge portions configured to permit motion without detachment of the patch.

When a layered patch device is used, samples may be obtained via microneedles that are fixed or removably secured to the skin-contacting layer of the patch. The microneedles may be about the size of a human hair and have an integrated microreservoir. The microneedle will be generally configured to painlessly penetrate the skin. The microneedles may be constructed out of silicon or other suitable metals and polymers, and may be about 10 µm to about 200 µm, about 50 µm to about 150 µm, or about 100 µm in diameter. In some instances, the microneedle will be designed to obtain blood samples. Here the microneedles may collect about 0.01 to about 1.0 microliter, about 0.05 to about 0.5 microliters, or about 0.1 to about 0.3 microliters of capillary blood. The microneedles may be deployable, injectable through the skin after placement of the patch on the patient's skin. The microneedles may be deployable simultaneously, or in subsets of the entire group, and may be deployed on demand, at a particular time event, and/or when an analysis, such as an assay analysis, produces specific results. The tips of the microneedles may be arranged in a single plane, or may lie in multiple planes. One or more of the microneedles may be straight or curved. The diameter of the microneedles may be consistent or may vary. The microneedles may be deployed into tumor tissue, such as skin cancer or other cancer close to the epidermal layer of the patient's skin.

In general, microfabrication processes that may be used in making the microneedles disclosed herein include lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, and lamination. Alternatively, the needles may be molded in silicon wafers and then plated using conventional wire cutting techniques with nickel, gold, titanium or various other biocompatible metals. In another variation, the needles may be fashioned from biopolymers.

Ingestible Devices

The ingestible device may be any one of the devices described above that has been modified for ingestion. Thus, the ingestible device may be a microchip or assay device having a coating or other component that protects it from premature degradation and/or contamination. The device or portions thereof may be made from ingredients included in conventional oral dosage forms. Such ingredients are known, or will be apparent, to those skilled in the art (see, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins).

Imaging Devices

The substance delivering device may also be used as an imaging device. The imaging device may be of any configuration described herein, so long as it delivers a contrast agent detectable by an imaging modality. Examples of imaging modalities include x-ray, CT, MRI, ultrasound, PET scan, fluoroscopy, and the like. Here the contrast agent is used to obtain structural or functional information about the target tissue. Contrast agents that may be employed include without limitation, barium sulfate, iodinated contrast agents, water, gadolinium, iron oxide, and fluorescent imaging agents. Exemplary iodinated contrast agents that may be delivered include, but are not limited to, diatrizoate, metrizoate, ioxaglate, iopamidol, iohexyl, ioxilan, iopromide, and iodixanol. Contrast agents that may be activated to indicate the presence of particular analytes may also be employed. As mentioned above, a port may also be included or removably secured to the device for imaging purposes.

II. Systems

In general, the systems will include a substance delivery device as herein described, e.g., a biopsy device, an assay device, a microchip device, an ingestible device, a patch device, an imaging device, or a combination thereof, and a deployment tool for delivery of the device to a target tissue. Any deployment tool may be used to deliver the device. The configuration of the deployment tool may depend on such factors as the type of device used, the route of delivery employed, and the particular target tissue. The deployment tool may be designed for delivering the device via any route. For example, the deployment tool may include features useful for delivery during open, laparoscopic, endoscopic, arthroscopic, percutaneous, and robotic procedures. In some variations, the deployment tool comprises a catheter/pusher assembly. In other variations, the deployment tool includes jaws.

The systems may also include a retrieval tool for removing the device from the target tissue. These retrieval tools may be formed to include suction, jaws, hooks, magnets, etc. to aid removal. In some variations, an energy source is provided in the systems to activate release of the substance contained within the reservoirs. In other variations, e.g., when an imaging device is part of the system, an imaging modality as previously described may be included in the system. Additional components, e.g., in vitro assays, may also be included to tailor the system.

Figure 7:
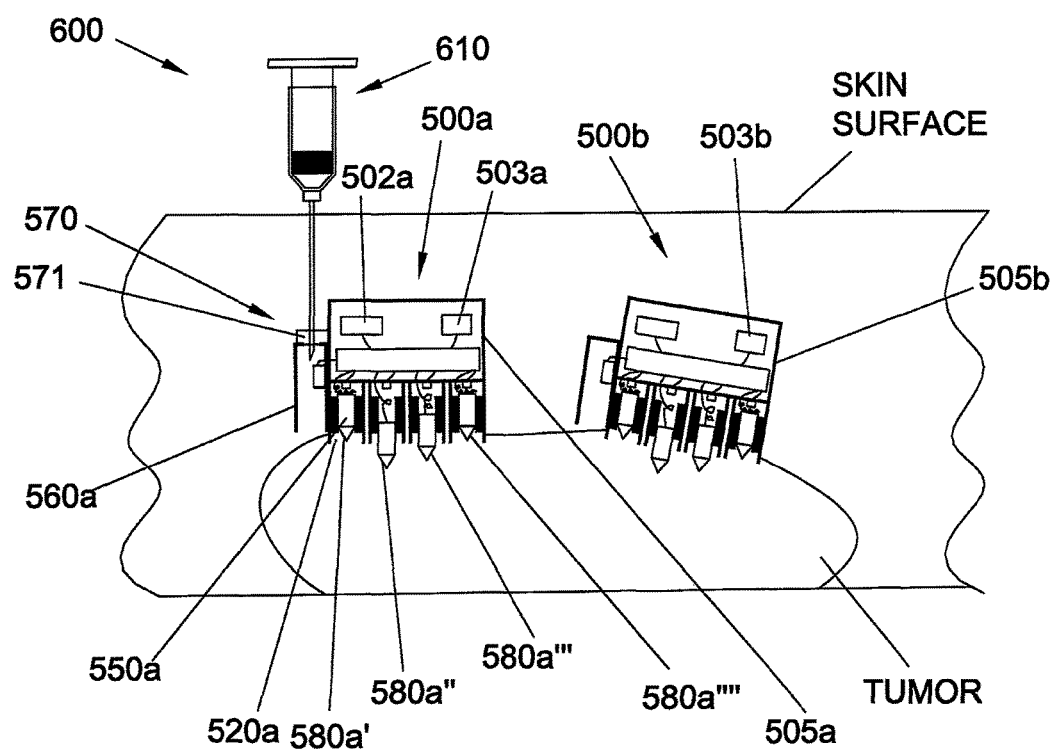
FIG. 7 illustrates an exemplary substance delivery system including two devices implanted in a single tumor and a percutaneous tool accessing one of the devices.

Referring to FIG. 7, a substance delivery system of the present invention is illustrated. System 600 includes substance delivery devices 500a and 500b, of similar construction to delivery device 500 of FIG. 5, with the same reference numbers used to refer to the same or like parts. Devices 500a and 500b each include a microcontroller, 501a and 501b respectively, which transmit and receive data from wireless transceiver 503a and 503b respectively. Wireless transceiver 503a and 503b are further configured to communicate with each other such that information obtained or produced from device 500a or 500b can be transmitted to the other. In the configuration of FIG. 7, devices 500a and 500b have been implanted below the skin of the patient at the site of a single tumor. In an alternative method, device 500a may be implanted in a first tumor, and device 500b may be implanted in a different tumor of the same patient. In another alternative method, device 500a may be implanted in a tumor and device 500b implanted in healthy tissue, such as to act as a control. Device 500a and 500b further include ingrowth assemblies 560a and 560b respectively. Ingrowth assembly 560a and 560b comprise a vessel configured to allow cells, such as cancer cells, to migrate into the vessel. In a preferred embodiment, the vessel is coated or otherwise includes a biologic growth factor such as epidermal growth factor (EGF). Numerous growth factors can be included in or on ingrowth assemblies 560a and 560b including but not limited to colony stimulating factor (CSF) and one or more cytokines such as SDF1-alpha. Each ingrowth assembly may receive the same or different growth factor than a different ingrowth assembly. Ingrowth assembly 560a may be removably attached to device 500a or may be a separate component, such as a separate implant assembly that include communication means, such as wired or wireless communication means to communicate information to one or more separate devices such as device 500a. Device 500a and/or device 500b (hereinafter device 500a only for simplicity) may include a second ingrowth assembly, such as to attract a different type of cells. Alternatively ingrowth assembly 560b may be configured to attract different cells, such as where one cell type is a housekeeping or control cell, used to confirm results or compare to results obtained from ingrowth assembly 560a, such as when ingrowth assembly 560a is configured to attract cancer cells.

The ingrowth assemblies may include an assay function or component, as has been described hereabove. Ingrowth assembly 560a of device 500a includes assay component 561 configured to produce data based on the cells that migrate into assembly 560a. In a preferred embodiment, assay component 561a performs an analysis of cancer cells such as to assess the invasiveness of a cancer. The data produced by assay component 561a may be used by the microcontroller to start, stop or modify the delivery of one or more agents by device 500a, such as to maintain or increase delivery of a therapeutic agent (e.g. chemotherapeutic) with confirmed benefit and/or decrease or stop delivery of a therapeutic agent with no confirmed benefit.

Device 500a further includes access port 570, containing a resealable membrane, septum 571 configured to be repeatedly accessed with a sharp tool such as a needle while maintaining a seal. System 600 further includes a percutaneous access tool, syringe 610 shown accessing port 570 through septum 571. Access port 570 can be used to deliver one or more agents into ingrowth assembly 560a, and/or to remove material, such as the migrated cells, from ingrowth assembly 560a. Alternatively or additionally, a similar access port can be integrated into or attached to another part of device 500a such as to add an agent to a reservoir of device 500a, or otherwise add or remove a material from device 500a.

Device 500a of system 600 further includes an electrode on the distal end of each reservoir. Reservoir 550a' includes electrode 580a', reservoir 550a'' includes electrode 580a'', reservoir 550a''' includes electrode 580a''', and reservoir 550a'''' includes electrode 580a''''. Each of the electrode 580a are configured to produce an electrical field in or about device 500a and/or the target tissue, a tumor as shown in FIG. 7, such as by delivery of current between one or more electrodes 580. Alternatively or additionally, device 550b may include one or more electrodes and current may be delivered between an electrode of device 500a and an electrode of device 500b. Alternatively or additionally, one or more electrodes may be included at a different location of reservoir 550a or device 500a, such as on or in chamber 520a, or on housing 505a. The energy delivered by one or more electrodes 580 may be based on the results of an analysis, such as an analysis performed by an assay component of device 500a. Electrodes 580 may be placed into the target tissue, such as in the tumor of FIG. 7, due to reservoir 580'' and 580''' having been previously advanced into the tumor as has been described in reference to FIG. 5. The electric fields generated by electrodes 580 may be used to enhance delivery of drug through iontophoresis and/or electroporation, drug delivery enhancement means well known to those of skill in the art. The electric fields generated may be an additional or alternative way to modify the actual amount of agent delivered, such as when device 500a delivers fluid at a continuous rate, but modifies the electric field produced by electrodes 580 to enhance or diminish fluid transfer through iontophoresis, or cellular uptake with electroporation.

III. Methods

1) Delivery and Retrieval

The devices described here may be delivered in any manner. For example, they may be delivered via an open surgical procedure, or by a minimally invasive procedure such as laparoscopy, endoscopy, arthroscopy, and catheter-based procedures. The devices may also be delivered percutaneously or topically. Delivery using a robotic device is also contemplated. Retrieval of the devices may occur via the same processes. An image of the target tissue, such as a tumor, may be performed prior to, during, or after use of the device. In a preferred embodiment, the device is applied to the patient's skin or implanted in the patient with image guidance. The devices of the present invention include one or more penetrating or advanceable members such as advanceable reservoirs. In a preferred embodiment, the penetrating or advanceable members penetrate or advance into tissue using image guidance, such as images created before or during penetration and/or advancement.

In general, the device including a microdose of a substance is delivered to a target tissue, e.g., by implantation into the target tissue, such as to perform a diagnostic and/or therapeutic procedure. The substance is locally delivered in a concentration adequate to result in a pharmacological effect. A sample from the target tissue such as a biopsy of the tissue, is then obtained. In one variation, the sample is obtained by the device that delivers the substance. In another variation, the sample is obtained via procedures such as percutaneous biopsy, open biopsy, needle aspiration, and the like. The sample tissue can then be subjected to various assays for evaluating the substance effect on the target tissue. For example, the sample may be subjected to genomic, proteomic, biochemical, and/or histopathological characterization.

2) Dosing

The devices described here deliver a microdose amount of a substance to a target tissue. A microdose amount may be from about 0.001 µg (or less) to about 1,000 µg or about 10,000 µg (or more) of the substance. Those of skill will readily appreciate that microdose levels may vary as a function of the specific substance employed, the target tissue, and/or the medical condition being treated.

The substance may be delivered in a controlled release, sustained release, delayed release, or pulsatile fashion. Delivery may also occur over any time period. For example, it may occur over a period of minutes to hours, days to weeks, weeks to months, or even one year or more.

3) Medical Conditions and Target Tissues

In some instances, the devices described here may be used to locally deliver a substance that is a candidate compound being evaluated for the treatment of a medical condition. In other instances, the substance itself is locally delivered to treat a medical condition. Medical conditions that are contemplated, include, but are not limited to, autoimmune conditions, cancer, cardiac conditions, gastrointestinal conditions, genitourinary conditions, hematologic conditions, infectious conditions, inflammatory conditions, ischemic conditions, neurologic conditions, obstetric conditions, orthopedic conditions, proliferative conditions, pulmonary conditions, and vascular conditions.

Furthermore, the devices may be delivered to any target tissue within the human body. Target tissues may include the neurologic tissues, pulmonary tissues, gastrointestinal tissues, genitourinary tissues, cardiac tissues, vascular tissues, muscle, bone, skin, and any fluids such as blood or lymph.

IV. Kits

The kits may provide one or more devices described here, e.g., one or more biopsy devices, microchip devices, assay devices, ingestible devices, patch devices, or imaging devices. The devices may include reservoirs that deliver the same substance or different substances. Likewise, the devices may include reservoirs that deliver the substances in the same or different microdoses. Any number and type of deployment tools, retrieval tools, energy components, and imaging devices may also be included. The kits may also contain additional in vitro assays for evaluating samples.

The kits may further include instructions for using the devices, tools, and/or assays contained therein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form would be a computer readable medium, e.g., diskette, CD, etc., on which the information has been recorded. In some variations, a website address may be provided that can be accessed via the internet to obtain the instructions.

The invention claimed is:

1. A microarray device comprising:
   an elongated support structure configured for administration within a needle, laparoscope, endoscope, arthroscope, or catheter,
   arrays along the length of the elongated support structure of multiple separate chambers being formed within the support structure, each chamber having a closed proximal end on the interior of the support structure and an open distal end on the outside of the support structure,
   each chamber comprising a solid matrix forming a reservoir containing microdoses of one or more therapeutic or diagnostic agents in the matrix, which are released into the open distal end only over a period between about one day and one week following insertion of the microarray device into tissue,
   wherein the open distal end of the chamber is configured to place the tissue in close proximity to the solid matrix from which agent is released, and
   wherein the device is configured to allow removal of the device at the same time as a sample of tissues, cells or fluid at the site of administration into which therapeutic or diagnostic agent is released from each chamber for separately sampling or analyzing of the tissue or cells adjacent to the distal end of the chambers.

2. The microarray device of claim 1 further comprising a deployment device configured for a laparoscopic, endoscopic, arthroscopic, or catheter-based procedure that separately extracts, samples or analyzes the tissue or cells at the sites of administration.

3. The microarray device of claim 1 wherein each of the reservoirs is loaded with different substances or different microdose amounts of the substances, which are released independently.

4. The microarray device of claim 1 wherein the reservoirs comprise biodegradable polymeric matrices which release agent as a function of diffusion or degradation.

5. The microarray device of claim 1 comprising a sensor selected from the group consisting of a strain gauge, an accelerometer, a temperature sensor, a pH sensor, a chemical sensor, a mechanical sensor, a radiation sensor and a physiologic sensor configured to assess one or more cell activities.

6. The microarray device of claim 1 wherein a biopsy device is used for extracting the microarray device or sampling or analyzing the tissue or cells adjacent to the distal end of the chambers.

7. The microarray device of claim 1 comprising an assay to detect analytes indicative of inflammation, to detect and analyze genes or their products which are over-expressed or over-active in cells undergoing unwanted proliferation, to detect infection or to detect abnormal cellular proliferation.

8. The microarray device of claim 1 comprising an imaging device.

9. The microarray device of claim 1 is in combination with a deployment or retrieval device or system.

10. The microarray device of claim 1 further comprising biopsy or assay devices, or a combination thereof, that separately sample or analyze the tissue or cells immediately adjacent to the reservoir.

11. The microarray device of claim 10 comprising a sensor selected from the group consisting of a strain gauge, an accelerometer, a temperature sensor, an optical sensor, a pH sensor, a chemical sensor, a mechanical sensor, a radiation sensor, a physiologic sensor configured to assess one or more cell activities and combinations of these sensors.

12. The microarray device of claim 10 comprising penetrating members.

13. The microarray device of claim 10 comprising a sensor or an assay to detect analytes indicative of inflammation, to detect and analyze genes or their products which are over-expressed or over-active in cells undergoing unwanted proliferation, to detect infection or to detect abnormal cellular proliferation, to detect an effect or response of the target tissue to the agent being released, or to visualize cellular or histological/histopathological changes in response to the agent being released.

14. The microarray device of claim 10 comprising an imaging device.

15. The microarray device of claim 10 in combination with a deployment or retrieval device.

16. A method for delivering therapeutic or diagnostic agent to cells or tissue in an individual, and extracting, sampling or analyzing the tissue or cells comprising:
   providing the microarray device of claim 1 and then separately extracting, sampling or analyzing the tissue or cells at the sites of administration.

17. The method of claim 16 comprising administering different amounts of the same therapeutic or diagnostic agent from the different reservoirs.

18. The method of claim 16 comprising administering different therapeutic or diagnostic agents from the different reservoirs.

19. The method of claim 16 comprising administering therapeutic or diagnostic agent in response to analysis or sampling of the cells or tissue.

20. The method of claim 16 further comprising determining sensitivity of the tissue or cells to a therapeutic agent.

21. A method for extracting tissue or cells comprising
providing the microarray device and the biopsy device of
  claim 10 and extracting cells or tissue immediately
  adjacent to the reservoir.

22. The microarray device of claim 3 further comprising a device configured to control release selected from the group consisting of a preprogrammed microprocessor, remote control, and one or more sensors.

23. The microarray device of claim 1, further comprising an imaging component for visualizing the device within the tissue.

\* \* \* \* \*